United States Patent [19]
Isahaya

[11] Patent Number: 5,604,335
[45] Date of Patent: Feb. 18, 1997

[54] MEASURING METHOD OF MASS CONCENTRATION OF SUSPENDED PARTICULATE MATTER IN GAS

[75] Inventor: Fumio Isahaya, Tokyo, Japan

[73] Assignee: Shibata Scientific Technology, Ltd., Tokyo, Japan

[21] Appl. No.: 283,525

[22] Filed: Aug. 1, 1994

[30]     Foreign Application Priority Data

Jul. 30, 1993   [JP]   Japan ..................... 5-189483

[51] Int. Cl.$^6$ ..................... G01H 1/06
[52] U.S. Cl. ............... 177/210 FP; 73/24.01; 73/24.03; 73/28.01
[58] Field of Search ............ 177/210 FP, 24.01, 177/24.03, 24.06, 28.01, 28.04

[56]            References Cited

U.S. PATENT DOCUMENTS

| 3,653,253 | 4/1972 | Olin ........................... 73/28.01 |
| 3,653,773 | 4/1972 | Childs ........................ 73/28.01 X |
| 4,391,338 | 7/1983 | Patashnick et al. ........ 177/210 FP |

*Primary Examiner*—Michael L. Gellner
*Assistant Examiner*—Randy W. Gibson
*Attorney, Agent, or Firm*—Antonelli, Terry, Stout & Kraus, LLP

[57]            ABSTRACT

The oscillation of an oscillator is automatically stopped during gas sampling, and the gas sampling is automatically stopped during the measurement of the frequency of the oscillator before and after the gas sampling, thereby making it possible to avoid the measurement error due to a change in resonance frequency by the effect of dynamic and static pressures applied to a filter paper holder mounted at the free end of the oscillator in the gas sampling, and to prevent the dislodgement and reentrainment of suspended particulates collected in the filter paper due to the oscillation acceleration. Accordingly, it is possible to accurately measure the mass of suspended particulates deposited on a filter paper compared with the conventional method in which the gas sampling and the measurement of the frequency are simultaneously and continuously performed while oscillating an oscillator. Concretely, a gas switching valve is provided between an oscillator and a pump, and a signal switch is provided between a sensor and an automatic gain control amplifier. With this construction, the oscillation of the oscillator is stopped during the gas sampling, and the gas sampling is stopped during the measurement of the frequency of the oscillator before and after the gas sampling on the basis of a synchronous control signal from a control processor.

6 Claims, 5 Drawing Sheets

MEASURING METHOD OF MASS CONCENTRATION OF SUSPENDED PARTICULATE MATTER IN GAS

BACKGROUND OF THE INVENTION

The present invention relates to a method of continuously measuring, in near real time, the mass concentration of particulates suspended in air, atmosphere or exhausted gas in various environments of work, production and life or point, area and mobile emission sources, using a relatively inexpensive monitor being simplified in handling, which is suitable for high level ambient air quality control and industrial hygiene management and quality control in industrial production process.

As a typical technique of measuring the mass concentration of particulates suspended in an ambient air or an exhausted gas in the above fields, there have been known the following four methods:

(1) Filter Paper Sampling Method (2) Beta Ray Attenuation Method (hereinafter, referred to as "BAM method")

(3) Quartz Crystal Oscillating Microbalance Method (hereinafter, referred to as "QCM method")

(4) Tapered Element Oscillating Microbalance Method (hereinafter, referred to as "TEOM method") (U.S. Pat. No. 4,391,338 filed Jul. 5, 1983; and Examined Japanese Patent Publication No. 1-45569 filed Oct. 4, 1989)

The filter paper sampling method shown in (1) includes the steps of filtering and sampling particulates suspended in atmospheric air or a gas with a filter paper medium, and weighing the incremental weight of the sampled particulates by a balance, thereby calculating the mass concentration. This is an excellent reference method; however, it has a disadvantage in that the sampling and weighing take lots of time and labor, thereby making it difficult to continuously and automatically measure the mass concentration in real time.

The BAM method shown in (2) includes the steps of filtering and sampling suspended particulates with a roll tape filter paper medium, irradiating beta rays to the sampled particulates, and measuring the change in the attenuation ratio of the beta rays, thereby calculating the mass concentration. This method enables the monitoring for a long period, about three months. However, from the viewpoint of safety, this method uses a radiation source with a low level radioactivity (generally, about 100 µCi or less) such as a radio-isotope $C^{14}$, which causes the following disadvantages. In general, it becomes difficult to collect the above suspended particulates in an amount sufficient to obtain the attenuation ratio of beta rays with necessary measurement accuracy, unless the sampling time is set at a large value, that is, about 1.0 hr. Moreover, the statistical measurement error becomes large, unless the measurement time for the attenuation ratio of beta rays is more than several minutes. For these reasons, it is possible to intermittently and automatically measure the average mass concentration for a long sampling time, that is, about 1.0 hr; however, it is difficult to continuously measure the mass concentration varied in a period shorter than the above sampling time. On the other hand, to improve the above measurement accuracy by enlarging the change in the attenuation ratio of beta rays to the utmost, it is required to reduce the filtration area (generally, about 1 $cm^2$) and to allow the sampled gas to collectively pass through the reduced filtration area at a high rate (generally, about 15 l/min). The filtration rate of gas is increased to a large extent of about 10 times as much as the allowable filtration rate (10 to 30 $cm^3$/s), thereby abnormally increasing the pressure loss of the filter paper medium. As a result, the measurement error tends to be easily generated by an abnormal phenomenon such as the bypass leak of the sampled gas, and the blow of dust through the filter paper medium.

The QCM method shown in (3) utilizes the shear oscillation mode of a circular disk-like AT cut quartz crystal oscillator. The natural frequency of the crystal oscillator is changed depending on the increase in the mass concentration of suspended particulates electrostatically deposited on the surface of the electrode of the crystal oscillator by an electrostatic dust collecting method. The change in the mass of the suspended particulates is detected, thus calculating the mass concentration. This OCM method had the following disadvantages. The principle of this method is based on the assumption that a deposition layer of the dust particles on the surface of the electrode becomes a uniform thin layer; however, actually, in the electrostatic dust collecting method used in this QCM method, the physical properties such as particle size distribution or electric resistivity of dust are changed, and thereby the thickness of the deposition layer becomes non-uniform; and further, since the high frequency oscillation acceleration (several MHz) of the quartz crystal is usually applied to the deposition layer, there occurs the dislodgement and reentrainment of dust from the deposition layer, thereby causing a large measurement error. Moreover, the holding capacity of the amount of the dust deposition on the electrode is extremely small (10 µg), so that it is required to frequently clean the electrode. The electrode is also worn by the above dust deposition, and the expensive quartz crystal must be frequently replaced; and a needle type electrode for electrostatic dust collection is degraded in capacity by the electric wear due to corona discharge, and which must be also frequently replaced. For these reasons, the QCM method is difficult to be used as the continuous monitoring method.

The TEOM method shown in (4) utilizes the so-called cantilever oscillator having a tapered bar element with a through hole which is changed in the axial sectional area, wherein the large diameter end is taken as the fixed end, and the small diameter end is taken as the free end. A filter paper holder is mounted at the free end. The suspended particulates are continuously filtered and sampled while continuously oscillating the filter paper holder, and the change in the reduced natural frequency of the oscillator with time depending on the change in the mass with time is detected, thus calculating the mass concentration. This is an excellent method capable of continuously and automatically measuring the mass concentration with a monitor in near real time. However, since the oscillator and the filter paper are oscillated while usually filtering the gas with the filter paper, the suspended particulates collected on the filter paper are usually applied with a dislodgement force due to the oscillation acceleration, thus causing the reentrainment of dust from the filter paper. Moreover, the filter paper is usually applied with dynamic and static forces due to the gas flow, the frequency is affected by causes other than the increase in mass, thus causing a measurement error. This will be concretely described as follows.

(1) Dislodgement of Particles from Filter Paper of Oscillator, or Mutual Adhesion between Particles Hereinafter, there will be described the relationship between the adhesive force and the dislodgement force due to oscillation acceleration, of a particle to and from an object or between particles (see H. Krupp and G. Sperling: Theory of Adhesion of Small Particles, J1' of Applied Physics, Vol. 37, No. 11, October 1966, p. 4176 to 4180).

In general, an adhesive force <f> of a particle adhering on an object is due to the so-called van der Waals force fvdw as an inter-molecular force acting between surfaces of points in close proximity to each other, or a capillary condensation force at the contact point. In the measurement method of the present invention, however, the latter may be negligible because the filter paper is usually heated at about 40° C. and the possibility that water or the like is condensed at the contact point between particles is low. As a result, the former, that is, the van der Waals force is dominate, and which is expressed as follows:

$$fvdw = z_0 Pvdw \, (d_1 d_2)/(d_1 + d_2) \quad (1)$$

where Pvdw is the van der Waals component of free energy attractive forces at the interface of adhesive area.

$$Pvdw = h\omega/8\pi z_0^3$$

where $h\omega$: Lifshitz-van der Walls constant, $z_0$: adhesive distance between the adherents, $d_1$: particle diameter, and $d_2$: diameter of the object on which the particle adheres.

The constant $h\omega$ differs depending on the physical properties of the particle and the object, and is in the range of about 0.5~9 eV=0.5~9×10⁻¹² erg. $z_0$ is about 1 Å=10⁻⁸ cm.

On the other hand, the dislodgement force fs applied to a particle adhering on an oscillated object due to oscillation acceleration is expressed as follows:

$$fs = (\pi d_1^3/6)\rho Am(2\pi f)^2 \quad (2)$$

where $\rho$: density of particle,

Am: maximum amplitude of free end of tuning fork prongs oscillated with sinewave, and fs: frequency.

Eventually, from the above two expressions (1) and (2), the relationship between the critical frequency fc in generation of dislodgement and dust particle diameter $d_1$ is expressed as follows:

$$fc = [z_0 Pvdw d_2/(d_1+d_2)/20.67 \, d_1^2 \rho Am]^{1/2} \quad (3)$$

Assuming that $z_0=10^{-8}$ cm, Pvdw=10⁸ dyne/cm², the apparent diameter of the filter $d_2=2$ μm, the density of dust particle $\rho=2$ g/cm³, and the maximum amplitude at the free end of the oscillator Am=30 μm, the relationship between the dust particle diameter $d_1$ and the critical frequency fc in generation of dislodgement is calculated on the basis of the above expression (3), which gives the result shown in Table 1.

TABLE 1

| $d_1$ (μm) | 1 | 5 | 10 |
|---|---|---|---|
| fc (Hz) | 3,094 | 3,024 | 1,155 |

The frequency of the oscillator type mass microbalance is in the range from about several hundreds to several thousands Hz, and the diameter of the target dust particle is in the range of about 10 μm or less. As a result, it is revealed that comparatively coarse particles each having a particle diameter of several μm among the dust particles collected on the oscillated filter paper tend to be dislodged and reentrained.

(2) Error of Frequency of Oscillator Affected by Dynamic and Static Pressure Applied to Filter Paper during Gas Sampling In the case that the resonance frequency of an oscillator during stoppage of sampling is approximately 2,000 Hz, by performing the gas sampling at a rate of about 1.5 l/min using a glass fibrous filter having an effective area of about 1 cm² there occurs a pressure loss of about several tens mmH$_2$O, resulting in the generation of an error of about 0.01 to 0.05 Hz. This error corresponds to the mass change of several μg, and therefore, it is not negligible.

SUMMARY OF THE INVENTION

An object of the present invention is to avoid the measurement error due to a change in resonance frequency by the effect of dynamic and static pressures applied to a filter paper holder mounted at the free end of an oscillator in the gas sampling, and to prevent the dislodgement and reentrainment of dust particles collected on a filter paper due to the oscillation acceleration.

The above object can be achieved, according to the present invention, by provision of a method of measuring the mass concentration of particulates suspended in a gas, including the steps of: filtering and sampling particulates suspended in a gas with a filter paper holder mounted at a free end of an oscillator; and measuring the frequency of the oscillator before and after the filtering and sampling; wherein the oscillation of the oscillator is stopped during the filtering and sampling, and the filtering and sampling are stopped during the measurement of the frequency of the oscillator.

DESCRIPTION OF THE PREFERRED EMBODIMENT

In a method of the present invention, the oscillation of an oscillator is stopped during gas sampling for preventing dust particles collected on a filter paper from being dislodged and reentrained by the oscillation acceleration of the oscillator, and further, the gas sampling is stopped during the measurement of the frequency for preventing a filter paper from being applied with dynamic and static forces, thereby eliminating the generation of errors or the change in the resonance frequency.

Figure 1:
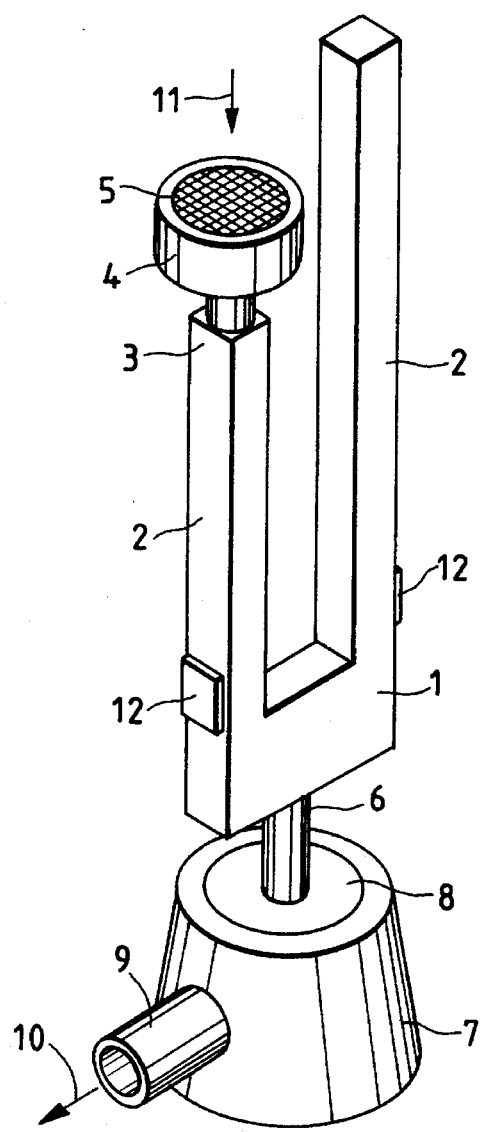
FIG. 1 is a perspective view showing the appearance of a tuning fork oscillator type microbalance mass concentration meter according to an embodiment of the present invention.
Figure 2:
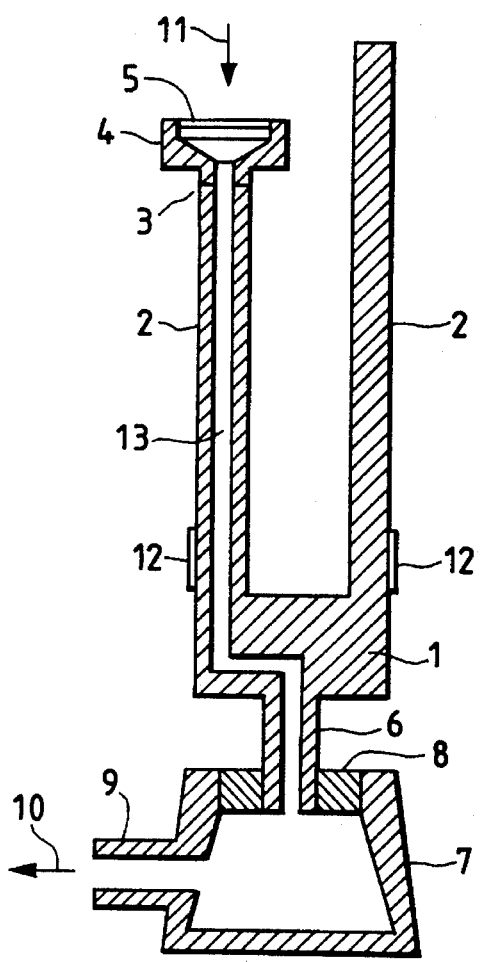
FIG. 2 is a vertical cross sectional view showing the structure of the mass concentration meter shown in FIG. 1.
Figure 3:
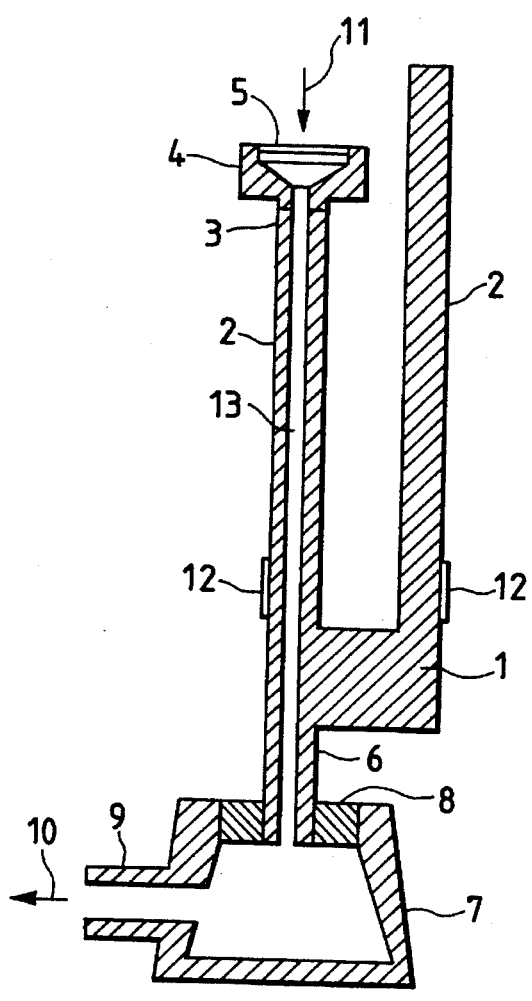
FIG. 3 is a vertical cross sectional view showing the structure of a mass concentration meter according to another embodiment of the present invention.
Figure 4:
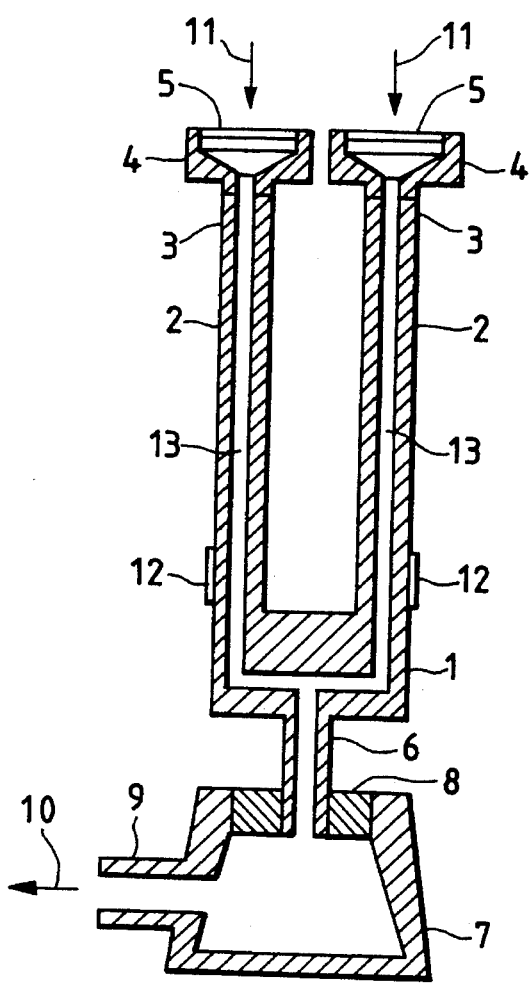
FIG. 4 is a vertical cross sectional view showing the structure of a mass concentration meter according to a further embodiment of the present invention.
Figure 5:
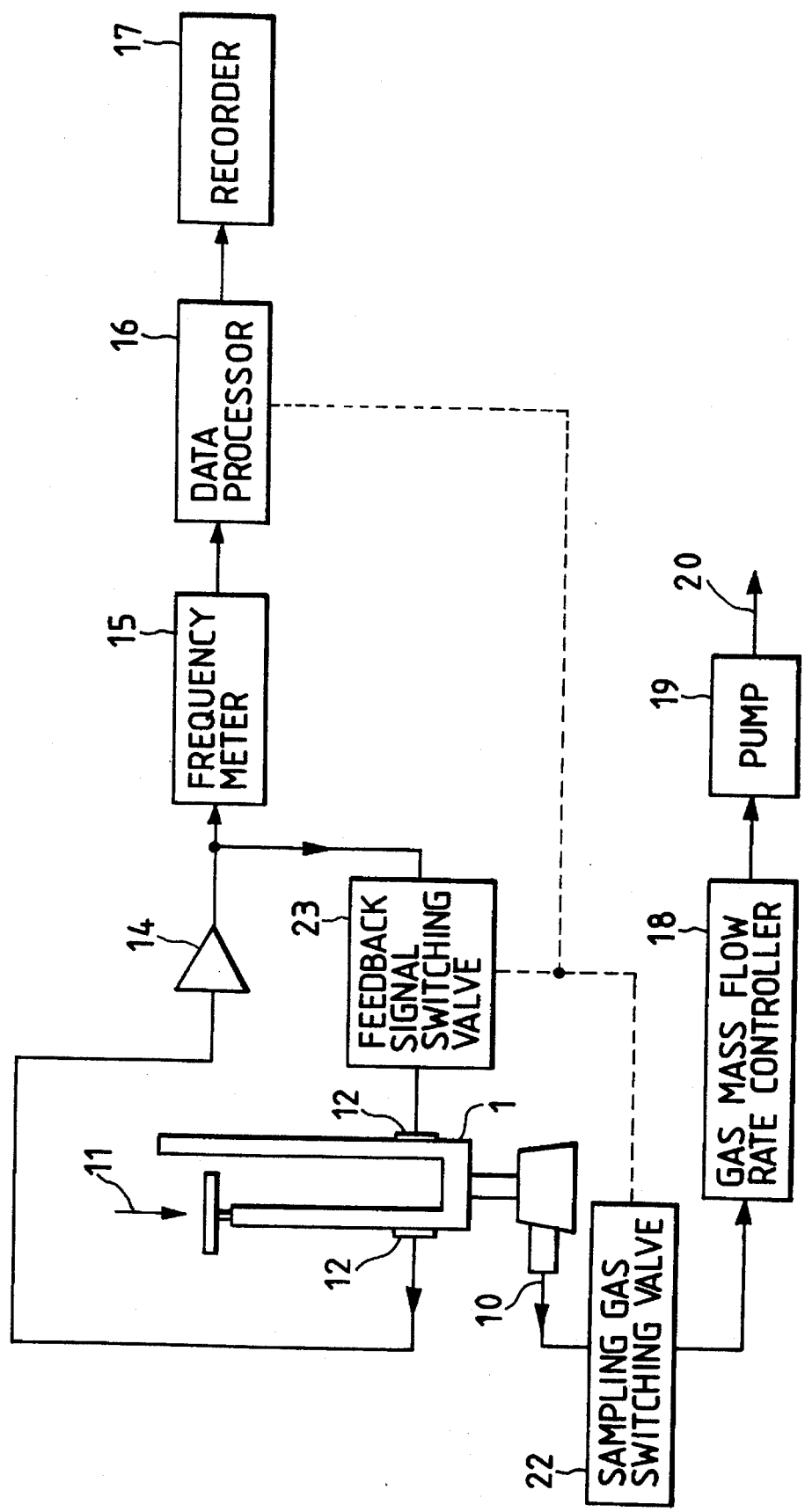
FIG. 5 is a block diagram showing a measuring system according to an embodiment of the present invention.
Figure 6:
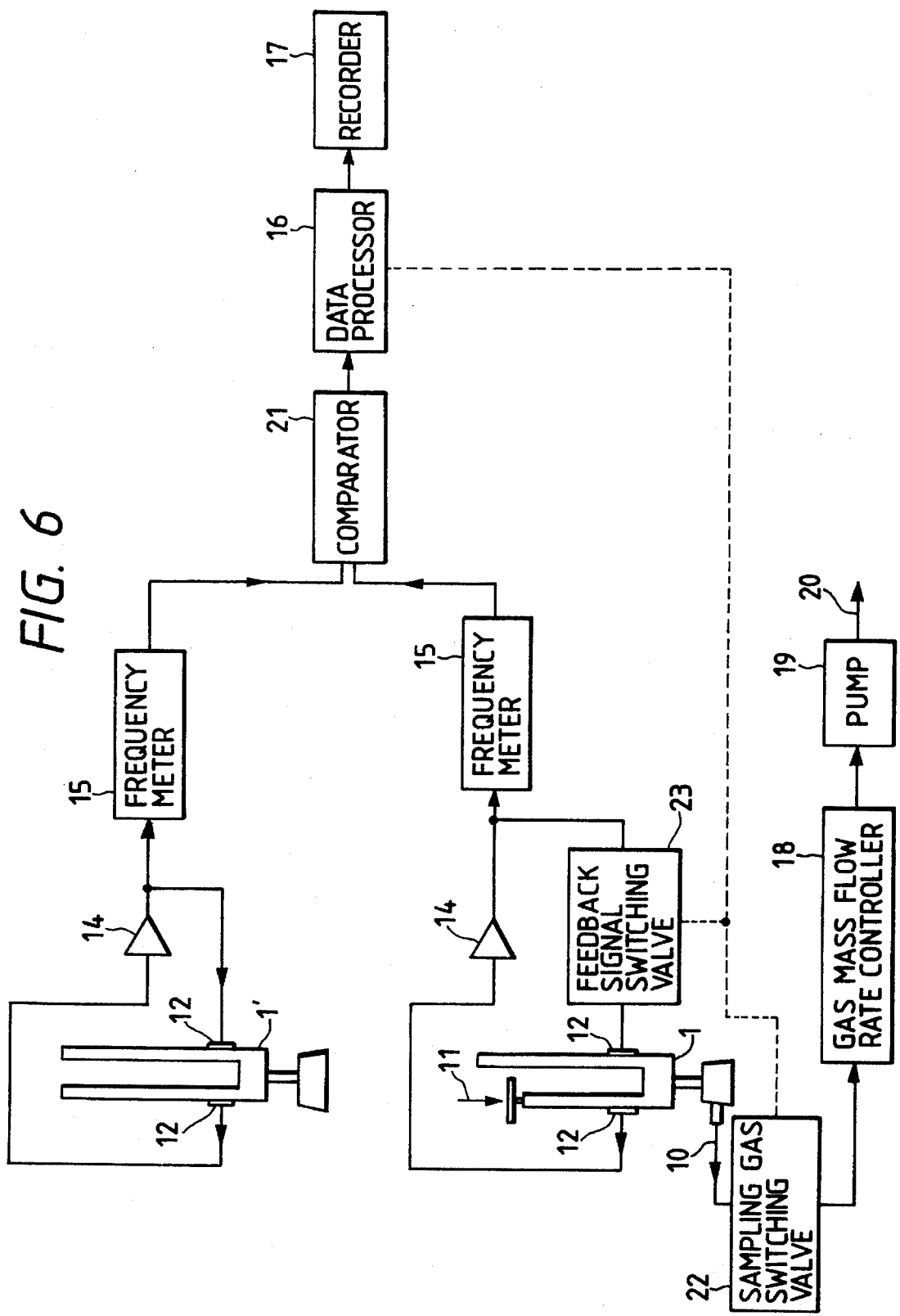
FIG. 6 is a block diagram showing a measuring system according to another embodiment of the present invention.
Figure 7:
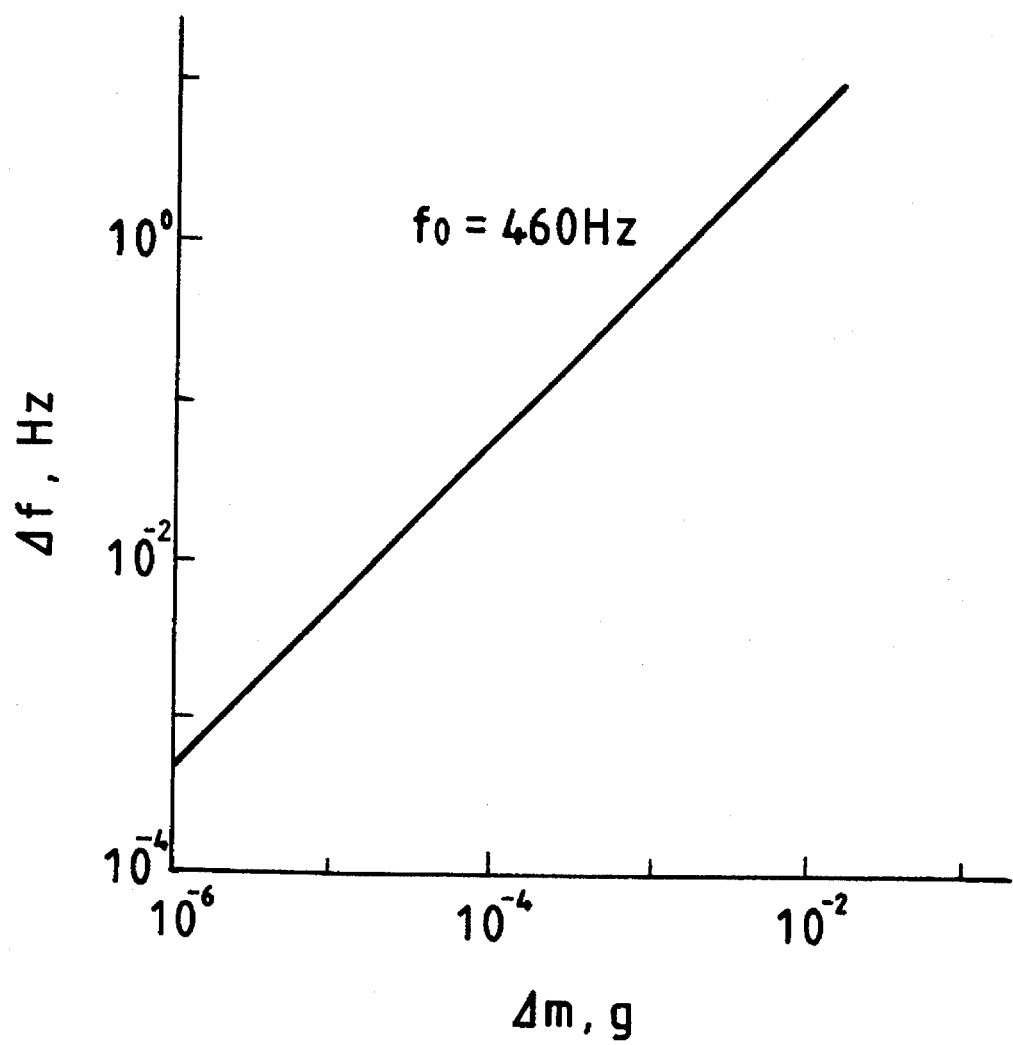
FIG. 7 is a diagram showing one example of measured result using the measuring apparatus of the present invention.

The present invention will be described in detail by way of embodiments using tuning fork oscillators. FIG. 1 is a perspective view showing the appearance of a tuning fork oscillator according to an embodiment; FIG. 2 is a cross sectional view of the oscillator; FIGS. 3 and 4 are a cross sectional views of tuning fork oscillators according to other embodiments; FIGS. 5 and 6 are block diagrams showing systems of performing gas sampling, resonant oscillation drive, and measuring oscillating frequency; and FIG. 7 is a diagram showing one example of the measured result.

Referring to FIG. 1, numeral 1 designates a tuning fork oscillator; and 2 is an oscillating prong. As for the two oscillating prongs 2, compared with one mounting a filter paper holder 4, the other is made slightly longer or attached with an additional mass such that the natural frequencies of both the prongs 2 are made to be substantially equal to each other thereby easily obtaining the resonance. A gas through hole 13 is axially provided in the oscillating prong 2 mounting the filter paper holder 4 along the center axis (see FIG. 2). The tuning fork oscillator 1 is fixed at the connecting knot (yoke) between both the oscillating prongs 2 on a supporting base 7 having a gas exhaust port 9 by a supporting rod 6 having a gas though hole by way of an oscillation-proof elastic member 8. An air or gas 11 containing suspended particulates is sucked in a specified amount by a pump 19 by way of a gas volume flow rate controller or a gas mass flow rate controller 18 (see FIGS. 5 or 6) connected to the gas exhaust port 9. The suspended particulates are filtered and collected on a filter paper 5 mounted on a filter paper holder 4. Only the gas is discharged as an exhausted gas 10 shown in FIG. 1, or as an exhausted gas 20 shown in FIGS. 5 and 6. FIGS. 2, 3 and 4 show the cross sectional views of the tuning fork oscillators of the embodiments of the present invention. In FIG. 2, the tuning fork oscillator 1 is supported by the supporting rod 6 at the axial symmetric portion. In FIG. 3, the tuning fork oscillator 1 is asymmetrically supported by the supporting rod 6 such that the gas through hole 13 is linearly disposed for reducing the pressure loss. In FIG. 4, gas though holes 13 are provided in both the oscillating prongs 2 of the tuning fork oscillator 1 for sampling a larger amount of gas, with the filter paper holders mounted on both the oscillating prongs 2, and the connecting knot between the oscillating prongs 2 is supported by the supporting rod 6 nearly at the axial symmetric portion. (in this case, the axial lengths of the two oscillation prongs 2 are made to be nearly equal to each other). Additionally, in FIG. 1, numeral 3 designates a free end of the tuning fork oscillator.

FIG. 5 shows a system for continuously measuring the mass concentration of particulates suspended in a gas in near real time using the above-described tuning fork oscillator. At first, the tuning fork oscillator is in the static state and has a free-free oscillation mode, and thereby it performs an extremely slightly natural resonant oscillation without a starting signal as an external force. One piezoelectric element 12 connected to the input side of an automatic gain control amplifier 14 detects the above natural resonant oscillation and generates a slight a.c sinewave electric signal. The signal is inputted in the automatic gain control amplifier 14, and is amplified with a high amplifying degree, which is applied to the other piezoelectric element 12 connected to the output side. As a result, the tuning fork oscillator 1 starts the self-excited oscillation with the natural resonance frequency. As the amplitude of the self-excited oscillation is increased, the output voltage of the piezoelectric element is increased, so that the amplifying degree of the automatic gain control amplifier is automatically reduced. Accordingly, the tuning fork oscillator 1 is usually resonated with a specified amplitude, and simultaneously a specified output of sinewave signal equal to the resonance frequency is usually generated from the automatic gain control amplifier 14. The electrical signal of the resonance frequency is transmitted to a frequency counter 15 to be counted, and is converted in the mass by a data processor 16 according to the following expression (4).

$$\Delta f = K_1 \{ 1/k_2^{1/2} - 1/(K_2 + \Delta m)^{1/2} \} \quad (4)$$

where $\Delta f$ is a reduction width of the resonance frequency of the oscillator corresponding to the weight increment $\Delta m$ of the filter in a specified sampling time interval (for example, several sec to several min); and $K_1$ and $K_2$ are constants determined by the elastic modulus, densities, geometrical forms and dimensions of the oscillator and filter paper holder. The mass concentration of the suspended particulates can be obtained on the basis of Am and the sampling gas flow rate corresponding to the sampling time interval.

The calculated result thus obtained is recorded and displayed by a recorder 17 by way of a data processor 16. In addition, numeral 18 designates a gas volume flow rate controller or a gas mass flow rate controller for usually sucking and exhausting a gas in a specified amount by the pump 19; 22 is a two-way valve or three-way valve for stopping the sampling gas when the change in the resonance frequencies of the oscillator before and after the specified gas sampling period, and which is automatically opened and closed on the basis of a control signal from the control processor; and 23 is a non-contact switch using, for example, a thyristor for switching a feedback signal of an automatic gain control amplifier 14 in synchronization with the control signal, which is automatically operated such that it is closed to stop the resonant oscillation of the oscillator during the gas sampling period, and is opened to perform the resonant oscillation during the measuring period of the resonance frequency.

FIG. 6 shows the embodiment wherein a comparator 21 is provided for measuring the difference in the resonance frequency between the tuning fork oscillator 1' for transmitting the reference frequency and the tuning fork oscillator 1 mounting the filter paper holder described above, thereby obtaining higher measurement accuracy.

FIG. 7 shows one example of the measured result according to the inventive method. As is apparent from this figure, it is possible to measure the mass over a wide range from a slight mass in the order of microgram to a relatively large mass in the order of gram.

In the above-described embodiments, the oscillating prong of the tuning fork oscillator is formed in a rectangular shape in section; however, it may be formed in a square, circular, elapse shape or the like in section. The oscillator is not limited to the tuning fork type, and may include cantilever prong type and the like. The material of the oscillator is generally selected as a constant modulus alloy; however, it may be selected from general industrial elastic materials including iron, stainless steel, aluminum alloy, titanium alloy, quartz crystal, ceramic, and engineering plastic.

What is claimed is:

1. A method of measuring the mass concentration of particulates suspended in a gas, comprising the steps of:

filtering and sampling particulates suspended in a gas with a filter paper holder mounted at a free end of an oscillator; and measuring the frequency of said oscillator before and after said filtering and sampling;

wherein the oscillation of said oscillator is stopped during said filtering and sampling.

2. A method of measuring the mass concentration of particulates suspended in a gas, comprising the steps of:

filtering and sampling particulates suspended in a gas with a filter paper holder mounted at a free end of an oscillator; and measuring the frequency of said oscillator before and after said filtering and sampling;

wherein said filtering and sampling are stopped during the measurement of the frequency of said oscillator.

3. A method of measuring the mass concentration of particulates suspended in a gas, comprising the steps of:

filtering and sampling particulates suspended in a gas with a filter paper holder mounted at a free end of an oscillator; and measuring the frequency of said oscillator before and after said filtering and sampling;

wherein the oscillation of said oscillator is stopped during said filtering and sampling, and said filtering and sampling are stopped during the measurement of the frequency of said oscillator.

4. A method of measuring the mass concentration of particulates suspended in a gas, comprising the steps of:

filtering and sampling particulates suspended in a gas with a filter paper holder mounted at a free end of an oscillator; and measuring the frequency of said oscillator before and after said filtering and sampling;

wherein a signal switch is provided in an urged signal circuit for said oscillator, and a control processor for operating said signal switch is provided, thereby stopping the oscillation of said oscillator by said signal switch during said gas sampling.

5. A method of measuring the mass concentration of particulates suspended in a gas, comprising the steps of:

filtering and sampling particulates suspended in a gas with a filter paper holder mounted at a free end of an oscillator; and measuring the frequency of said oscillator before and after said filtering and sampling;

wherein a gas switching valve is provided in a gas sampling circuit communicated to said holder, and a control processor for operating said gas switching valve, thereby automatically stopping said gas sampling by the operation of said gas switching valve during the measurement of the frequency of said oscillator.

6. A method of measuring the mass concentration of particulates suspended in a gas, comprising the steps of:

filtering and sampling particulates suspended in a gas with a filter paper holder mounted at a free end of an oscillator; and measuring the frequency of said oscillator before and after said filtering and sampling;

wherein a signal switch is provided in an urged circuit for said oscillator, a gas switching valve is provided in a gas sampling circuit communicated to said filter paper holder, and a control processor for operating said signal switch and said gas switching valve, thereby stopping the oscillation of said oscillator by said signal switch during said gas sampling, and automatically stopping said gas sampling by the operation of said gas switching valve during the measurement of the frequency of said oscillator before and after said gas sampling.

* * * * *